United States Patent [19]

Van Cott et al.

[11] Patent Number: 4,988,620

[45] Date of Patent: Jan. 29, 1991

[54] METHOD FOR PRODUCING THE FNUDI RESTRICTION ENDONUCLEASE AND METHYLASE

[75] Inventors: Elizabeth M. Van Cott, Salem; Geoffrey G. Wilson, Boxford, both of Mass.

[73] Assignee: New England Biolabs, Inc., Beverly, Mass.

[21] Appl. No.: 134,234

[22] Filed: Dec. 17, 1987

[51] Int. Cl.$^5$ .................. C12N 9/22; C12N 1/21; C12N 15/52

[52] U.S. Cl. ..................... 435/199; 435/252.33; 435/320.1; 435/172.3; 435/29; 435/73; 435/80; 435/82; 536/27

[58] Field of Search ............ 435/172.3, 199, 320, 435/252.3, 252.33; 935/29, 73, 80, 82; 536/27

[56] References Cited

FOREIGN PATENT DOCUMENTS 0193413 3/1986 European Pat. Off. .
0248678 9/1987 European Pat. Off. .

OTHER PUBLICATIONS

Mann et al., Gene 3: 97-112 (1978).
Kosykh et al., Molec gen. Genet, 178: 717-718 (1980).
Walder et al., Proc. Nat. Acad. Sci. USA 78 1503-1507 (1981).
Bougueleret et al., Nucleic Acids Res. 12:3659-3676 (1984).
Gingeras and Brooks, Proc. Natl. Acad. Sci. USA 80: 402-406 (1983).
Theriault and Roy, Gene 19:355-359 (1982).
Blumenthal et al., J. Bacteriol. 164:501-509 (1985).
Kiss et al., Nucleic Acids Res. 13:6403-6421 (1985).
Szomolanyi et al., Gene 10:219-225 (1980).
Janulaitis et al., Gene 20: 197-204, (1982).
Kiss and Baldauf, Gene 21:111-119 (1983).
Walder et al., J. Biol. Chem. 258: 1235-1241 (1983).
Raleigh and Wilson, Proc. Natl. Acad. Sci. USA 83:9070-9074, (1986).
Lui et al., Nucleic Acids Res. 6:1-15 (1979).
Birnboin and Doly, Nucleic Acids Res. 7:1513 (1979).
Greene, P. J. et al. (1981), J. Biol. Chem. 256(5), 2143-2153.
Newman, A. K. et al. (1981), J. Biol. Chem. 256(5), 2131-2139.
Schoner, B. et al. (1983) Gene 24, 227-236.
Walder, R. Y. et al. (1984), J. Biol. Chem. 259 (12), 8015-8026.
Lunnen, K. D. et al. (1988) Gene 74, 24-32.
Wilson, G. G. (1988) Trends in Genetics 4(11), 314-318.
Wilson, G. G. (1988) Gene 74, 281-289.

*Primary Examiner*—Elizabeth C. Weimar
*Assistant Examiner*—Charles L. Patterson
*Attorney, Agent, or Firm*—Gregory D. Williams; David G. Conlin

[57] ABSTRACT

The present invention is directed to a method for cloning and producing the FnuDI restriction endonuclease by (1) introducing the restriction endonuclease gene from *F. nucleatum* D into a host whereby the restriction gene is expressed; (2) fermenting the host which contains the vector encoding and expressing the FnuDI restriction endonuclease, and (3) purifying the FnuDI restriction endonuclease from the fermented host which contains the vector encoding and expressing the FnuDI restriction endonuclease activity.

8 Claims, 3 Drawing Sheets

METHOD FOR PRODUCING THE FNUDI RESTRICTION ENDONUCLEASE AND METHYLASE

BACKGROUND OF THE INVENTION

The present invention relates to clones for the FnuDI restriction endonuclease and modification methylase, and to the production of these enzymes from the clones.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the sequence. Different restriction endonucleases have affinity for different recognition sequences. Over one hundred different restriction endonucleases have been identified among many hundreds of bacterial species that have been examined to date.

Bacteria usually possess only a small number restriction endonucleases per species. The endonucleases are named according to the bacteria from which they are derived. Thus, the species Haemophilus aegyptius, for example synthesizes 3 different restriction endonucleases, named HaeI, HaeII and HaeIII. These enzymes recognize and cleave the sequences (AT)GGCC(AT), PuGCGCPy and GGCC respectively. Escherichia coli RY13, on the other hand, synthesizes only one enzyme, EcoRI, which recognizes the sequence GAATTC.

While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by binding to infecting DNA molecule and cleaving them each time that the recognition sequence occurs. The disintegration that results inactivates many of the infecting genes and renders the DNA susceptible to further degradation by exonucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer bound or cleaved by the restriction endonuclease. The DNA of a bacterial cell is always fully modified, by virtue of the activity of its modification methylase and it is therefore completely insensitive to the presence of the endogenous restriction endonuclease. It is only unmodified, and therefore identifiably foreign, DNA that is sensitive to restriction endonuclease recognition and attack.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted, majority, of clones are destroyed while the desirable, rare, clones survive.

Type II restriction-modification systems are being cloned with increasing frequency. The first cloned systems used bacteriophage infection as a means of identifying or selecting restriction endonuclease clones (HhaII: Mann et al , Gene 3: 97-112, (1978); EcoRII: Kosykh et al., Molec. gen. Genet 178: 717-719, (1980); PstI: Walder et al., Proc. Nat. Acad. Sci. USA 78 1503-1507, (1981)). Since the presence of restriction-modification systems in bacteria enables them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into E. coli cloning plasmids (EcoRV: Bougueleret et al., Nucleic Acids Res. 12:3659-3676, (1984); PaeR7: Gingeras and Brooks, Proc. Natl. Acad. Sci. USA 80:402-406, (1983); Theriault and Roy, Gene 19:355-359, (1982); PvuII: Blumenthal et al., J.Bacteriol. 164:501-509, (1985)).

A third approach, and one that is being used to clone a growing number of systems, involves selecting for an active methylase gene referring to our patent application No. 707079 and (BsuRI: Kiss et al., Nucleic Acids Res. 13:6403-6421, (1985)). Since restriction and modification genes tend to be closely linked, clones containing both genes can often be isolated by selecting for just the one gene. Selection for methylation activity does not always yield a complete restriction-modification system however, but instead sometimes yields only the methylase gene (BspRI: Szomolanyi et al., Gene 10:219-225, (1980); BcnI: Janulaitis et al, Gene 20: 197-204 (1982); BsuRI: Kiss and Baldauf, Gene 21: 111-119, (1983); and MspI: Walder et al., J Biol. Chem. 258:1235-1241, (1983).

A potential obstacle to cloning restriction-modification genes lies in trying to introduce the endonuclease gene into a host not already protected by modification. If the methylase gene and endonuclease gene are introduced together as a single clone, the methylase must protectively modify the host DNA before the endonuclease has the opportunity to cleave it. On occasion, therefore, it might only be possible to clone the genes sequentially, methylase first then endonuclease. Another obstacle to cloning restriction-modification systems lies in the discovery that some strains of E.coli react adversely to cytosine modification; they possess systems that destroy DNA containing methylated cytosine (Raleigh and Wilson, Proc. Natl. Acad. Sci., USA 83:9070-9074, (1986)). Cytosine-specific methylase genes cannot be cloned easily into these strains, either on their own, or together with their corresponding endonuclease genes. To avoid this problem it is necessary to use mutant strains of *E.coli* (McrA− and McrB−) in which these systems are defective.

Because purified restriction endonucleases, and to a lesser extent, modification methylases, are useful tools for characterizing and rearranging DNA in the laboratory, there is a commercial incentive to obtain strains of bacteria through recombinant DNA techniques that synthesize these enzymes in abundance. Such strains would be useful because they would simplify the task of purification as well as providing the means for production in commercially useful amounts.

SUMMARY OF THE INVENTION

In accordance with the present invention there is provided a clone containing the genes for the FnuDI restriction endonuclease and modification methylase derived from *Fusobacterium nucleatum* D, as well as related methods for the production of the enzymes. More specifically, this invention relates to clones which express the restriction endonuclease FnuDI, an enzyme which recognizes the DNA sequence GGCC and cleaves between the G and C. See Lui, A. C. P., McBride, B. C., Vovis, G. F. and Smith, M., Nucleic Acids Res. 6:1-15, (1979), the disclosure of which is hereby incorporated by reference herein. FnuDI restriction endonuclease produced in accordance with the present invention is free of the contaminanting FnuDII and FnuDIII endonucleases present in *F.nucleatum* D.

The preferred method for cloning this enzyme comprises forming a library containing the DNA from *F.nucleatum* D, isolating those clones which contain DNA coding for the FnuDI modification methylase and screening among these to identify those that also contain the FnuDI restriction endonuclease gene.

DETAILED DESCRIPTION OF THE INVENTION

The present invention relates to clones of the FnuDI restriction and modification genes, as well to the restriction endonuclease FnuDI produced from such clones. The FnuDI genes are cloned by a method which takes advantage of the fact that certain clones which are selected on the basis of containing and expressing the FnuDI modification methylase gene also contain the FnuDI restriction gene. The DNA of such clones is resistant to digestion by the FnuDI restriction endonuclease and the HaeIII restriction endonuclease. The resistance to digestion affords a means for selectively isolating clones encoding the FnuDI methylase and restriction endonuclease.

Figure 1:
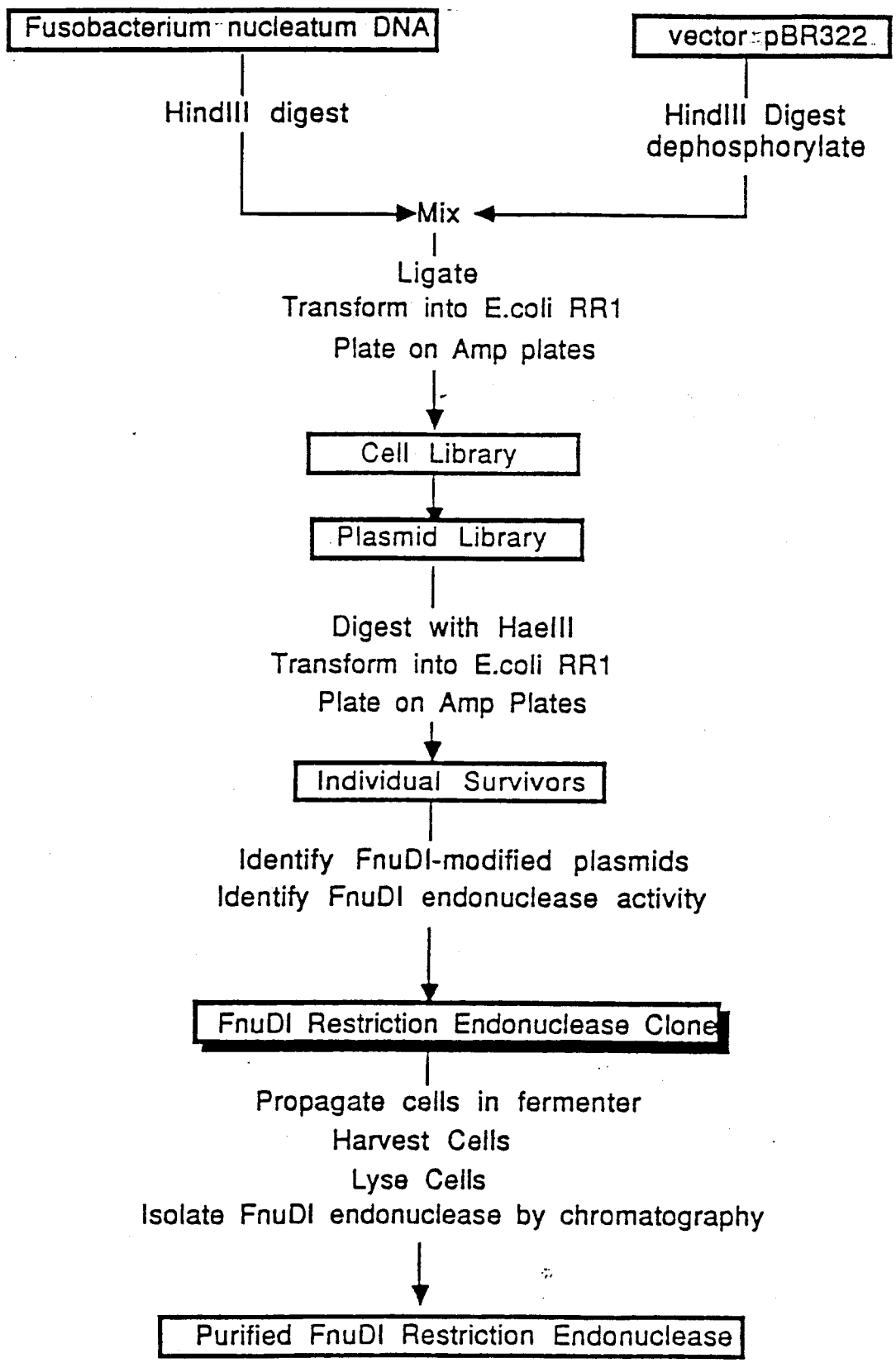
FIG. 1 illustrates the scheme for cloning and producing the FnuDI restriction endonuclease.
Figure 2:
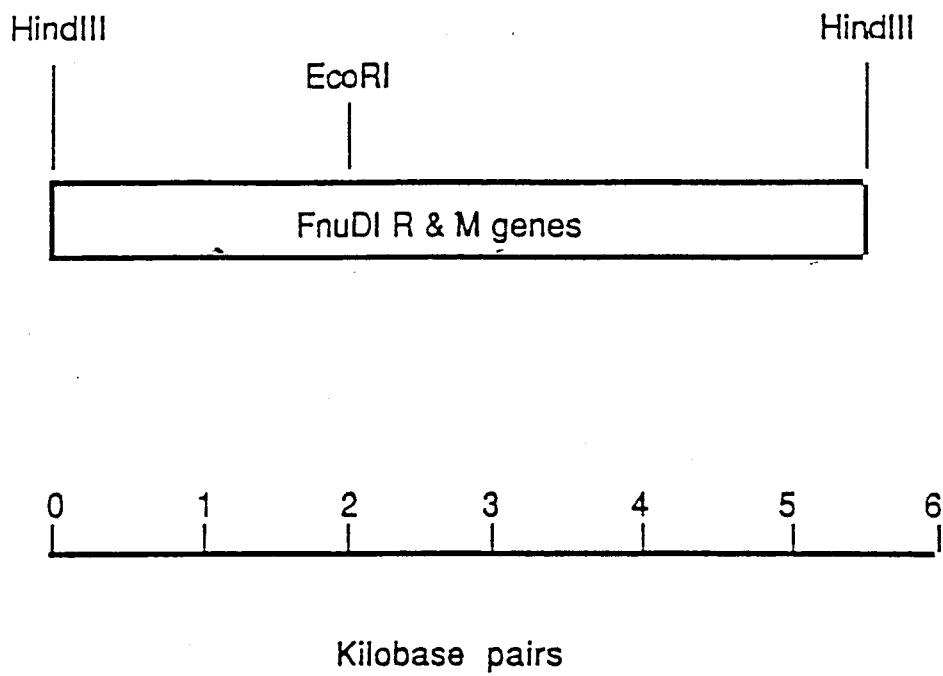
FIG. 2 is a restriction map of a 5.5 Kb HindIII fragment of *F.nucleatum* D DNA that encodes the FnuDI restriction endonuclease and modification methylase. The fragment was cloned into the HindIII site of pBR322 (ATCC 37017) to create pFnuDIRM 2-33, then it was transferred into the HindIII site of pUC19 (ATCC 37254) to create pFnuDIRM 102-1.

The method described herein by which the FnuDI restriction gene and methylase gene are preferably cloned and expressed are illustrated in FIG. 1, and they include the following steps:

1. The DNA of *Fusobacterium nucleatum* D is purified. *F.nucleatum* D has been described by Lui et al, supra, and was provided to us by Dr. Michael Smith, Dept. of Biochemistry, Faculty of Medicine, The University of British Columbia, Vancouver, Canada.
2. The DNA is digested with a restriction endonuclease such as HindIII.
3. The digested DNA is ligated to a cloning vector such as pBR322 (ATCC 37017), that contains one or more FnuDI sites. The ligated DNA is transformed into an appropriate host such as Escherichia coli strain RR1 (ATCC 31343).
4. The transformed mixture is plated onto media selective for transformed cells, such as the antibiotic ampicillin. After incubation, the transformed colonies are collected together into a single culture, the cell library.
5. The recombinant plasmids are purified in toto from the cell library to make the plasmid library.
6. The plasmid library is digested to completion with the FnuDI restriction endonuclease, or with an equivalent endonuclease, such as HaeIII, from *Haemophilus haemolyticus*. FnuDI (or HaeIII) digestion differentially destroys unmodified, non-methylase-containing, clones, increasing the relative frequency of FnuDI methylase clones.
7. The digested plasmid library is transformed back into an appropriate host such as *E.coli* RR1 , and transformants are recovered by plating onto selective media. The colonies are picked and their DNA is analyzed for the presence of the FnuDI modification gene: the plasmids that they carry are purified and incubated with the FnuDI (or HaeIII) restriction endonuclease to determine whether they are resistant to digestion. Total cellular DNA (chromosomal and plasmid) is also purified and incubated with the FnuDI (or HaeIII) restriction endonuclease. The DNA of clones that carry the FnuDI modification gene should be fully modified, and both plasmid DNA and total DNA should be substantially resistant to digestion.
8. Clones carrying the FnuDI restriction endonuclease are identified by preparing cell extracts of the FnuDI methylase clones, identified in step 8, and assaying the extracts for FnuDI restriction endonuclease activity.
9. The quantity of FnuDI restriction endonuclease produced by the clones may be increased by elevating the gene dosage, through the use of high copy number vectors, and by elevating the transcription rate, through the use of highly active, exogenous promotors.
10. The FnuDI restriction endonuclease may be produced from clones carrying the FnuDI restriction and modification genes by propagation in a fermenter in a rich medium containing ampicillin. The cells are collected by centrifugation and disrupted by sonication to produce a crude cell extract containing the FnuDI restriction endonuclease activity.
11. The crude cell extract containing the FnuDI restriction endonuclease activity is purified by standard protein purification techniques such as affinitychromatography an ion-exchange chromatography.

Although the above-outlined steps represent the preferred mode for practicing the present invention, it will be apparent to those skilled in the art that the above described approach can vary in accordance with techniques known in the art. The following example is given to illustrate embodiments of the present invention as it is presently preferred to practice. It will be understood that this example is illustrative, and that the invention is not to be considered as restricted thereto except as indicated in the appended claims.

EXAMPLE

Cloning of FnuDI Restriction Endonuclease Gene

1. DNA purification: 10 g of frozen *Fusobacterium nucleatum* D cells were thawed on ice for 1 hour then resuspended in 20 ml of 25% sucrose, 50mM Tris pH 8.0. 10 ml of 0.25M EDTA pH 8.0, and 6 ml of 10 mg/ml lysozyme in 0.25M Tris pH 8.0 were added. The suspension was kept on ice for 2 hours, then lysed by the addition of 24 ml of 1% Triton X-100, 50 mM Tris pH 8.0, 67 mM EDTA and 5 ml of 10% SDS. The solution was extracted with 70 ml of phenol, (previously equilibrated with 0.5M Tris pH 8.0), and 60 ml of Chloroform. The emulsion was centrifuged at 10K rpm for 30 minutes to separate the phases. The viscous upper phase was transferred to a new bottle and extracted with phenol and chloroform once more. The emulsion was again centrifuged then the upper phase was dialyzed against four changes of DNA buffer (10 mM Tris pH 8.0, 1 mM EDTA). The dialyzed solution was then digested with RNase at a final concentration of 200 ug/ml for 1 hour at 37° C. The DNA was then precipitated by the addition of 5M NaCl to a final concentration of 0.4M, and 0.55 volumes of isopropyl alcohol. The precipitated DNA was spooled onto a glass rod, air-dried, then dissolved in DNA buffer to a concentration of approximately 300 ug/ml and stored at 4° C.

2. Digestion of DNA: 30 ug of *F.nucleatum* D DNA was diluted into 300 ul of restriction endonuclease digestion buffer (10mM Tris pH 7.5, 10 mM MgCl$_2$, 10 mM mercaptoethanol, 50 mM NaCl). 60 units of HindIII restriction endonuclease were added and the solution was incubated at 37° C. for 2 hr. Digestion was terminated by heating to 72° C. for 12 minutes.

3. Ligation and transformation: 6 ug (60 ul) of HindIII-digested *F.nucleatum* D DNA was mixed with 3 ug (30 ul) of HindIII-cleaved and dephosphorylated pBR322 (ATCC 37017). 20 ul of 10 X ligation buffer (500 mM Tris pH 7.5, 100 mM MgCl$_2$, 100 mM DTT, 5 mM ATP), and 90 ul of sterile distilled water were added to bring the volume to 200 ul. 7.5 ul of T4 DNA ligase was added and the solution was incubated at 17° C. for 4 hours. The solution was sterilized by extraction with 20 ul of chloroform, then clarified by microcentifugation for 15 sec. 100 ul of the ligation solution was mixed with 800 ul of SSC/CaCl$_2$ (50 mM NaCl, 5 mM Na$_3$Citrate, 67 mM CaCl$_2$) and 1.7 ml of ice-cold, competent *E.coli* RR1 (ATCC 31343) cells were added. The solution was incubated at 44° C. for 4 mins, then 10 ml of Luria-broth (L-broth) was added and incubation was continued at 37° C. for 3 hr.

4. Cell Library: The transformed culture was gently centrifuged, the supernatant was discarded and the cells were resuspended in approximately 1.2 ml of L-broth. The resuspended cells were plated in approximately 200 ul portions onto 8 Luria-agar (L-agar) plates containing 100 ug/ml ampicillin. The plates were incubated overnight at 37° C. The transformed cells that grew up on the surfaces of the plates were collected together by flooding each of the plates with 2 5 ml of 10 mM Tris pH 7.5, 10 mM MgCl$_2$, scraping the colonies together, and pooling the suspensions into a single tube.

5. Plasmid Library: 2.0 ml of the cell library was inoculated into 500 ml of L-broth containing 100 ug/ml ampicillin. The culture was shaken overnight at 37° C. then centrifuged at 4K rpm for 5 minutes. The supernatant was discarded and the cell pellet was resuspended in 10 ml of 25% sucrose, 50 mM Tris pH 8.0, at room temperature. 5 ml of 0.25M EDTA, pH 8.0, and 3 ml of 10 mg/ml lysozyme in 0.25M Tris pH 8.0 were added. The solution was kept on ice for 1 hour, then 12 ml of 1% Triton X-100, 50 mM Tris pH 8.0, 67 mM EDTA was added and the suspension was gently swirled to induce cell lysis.

The lysed mixture was transferred to a 50 ml tube and centrifuged for 45 min. at 17K rpm, 4° C. The supernatant was removed with a pipette. 20.0 gm of solid CsCl was weighed into a 50 ml plastic screw-cap tube and 22.0 gm of supernatant was pipetted into the tube and mixed. 1.0 ml of 5 mg/ml ethidium bromide in 10 mM Tris pH 8.0, 100 mM NaCl, 1 mM EDTA was added. The solution was transferred to two ⅝ in.×3 in. centrifuge tubes and spun in a Beckman Ti70 rotor for 42 hours at 44K rpm, 17° C. To collect the plasmids, the tubes were opened, illuminated with ultraviolet light, and the lower of the two fluorescent bands was collected by syringe. The lower band from each tube was combined and the ethidium bromide was removed by extracting four times with an equal volume of water-saturated, ice-cold N-Butanol.

The extracted solution was dialyzed against 4 changes of DNA buffer, then the nucleic acid was precipitated by the addition of 2 vols. of isopropanol and sufficient 5M NaCl to reach a final concentration of 0.4M. The solution was stored overnight at −20° C. then centrifuged for 15 min. at 15K rpm, 0° C. The supernatant was discarded, the pellet was air-dried for 15 min. then dissolved in 500 ul of 10 mM Tris pH 7.5, 1 mM EDTA and stored at −20° C. The plasmid DNA concentration was found to be approximately 100 ug/ml.

6. Digestion of the Plasmid Library: 6 ug (60 ul) of the plasmid library was diluted into 450 ul of restriction endonuclease digestion buffer (section 2). 60 units (7.5 ul) of HaeIII restriction endonuclease were added and the tube was incubated at 37° C. for 1 hr. The reaction was terminated by heating to 72° C. for 12 minutes.

7. Transformation: 12.5 ul (0.18 ug) aliquots of the digested library were mixed with 100 ul of SSC/CaCl$_2$ (section 3) and 200 ul of ice-cold, competent, *E.coli* RR1. The mixtures were warmed to 42° C. for 3 min. then plated onto L-agar plates containing 100 ug/ml ampicillin. The plates was incubated overnight at 37° C. HaeIII digestion was found to reduce the number of transformants by a factor of approximately 10³. Fourteen colonies were picked from the survivors of the HaeIII digestion; each was inoculated into 10 ml of L-broth containing ampicillin, to prepare a miniculture, and streaked onto an L-agar plate containing ampicillin, to prepare a master stock.

8. Analysis of surviving individuals: Fourteen of the surviving colonies described in section 7 were grown into 10 ml cultures and the plasmids that they carried were prepared by the following miniprep purification procedure, adapted from the method of Birnboin and Doly, Nucleic Acids Res. 7: 1513 (1979).

Miniprep Procedure: Each culture was centrifuged at 8K rpm for 5 minutes; the supernatant was discarded and the cell pellet was resuspended in 1.0 ml of 25 mM Tris, 10 mM EDTA, 50 mM glucose, pH 8.0, containing 1 mg/ml lysozyme. After 10 minutes at room temperature, 2.0 ml of 0.2M NaOH, 1% SDS was added to each tube and the tubes were shaken to lyse the cells, then placed on ice. Once the solutions had cleared, 1.5 ml of 3M sodium acetate, pH 4.8, was added to each and shaken. The precipitates that formed were spun down at 15K rpm, 4° C. for 10 minutes. Each supernatant was poured into a centrifuge tube containing 3 ml of isopropanol and mixed. After 10 minutes at room temperature, the tubes were spun at 15K rpm for 10 minutes to pellet the precipitated nucleic acids. The supernatants were discarded and the pellets were air-dried at room temperature for 30 minutes. Once dry, the pellets were resuspended in 850 ul of 10 mM Tris, 1 mM EDTA, pH 8.0. 75 ul of 5M NaCl was added to each and the solutions were transferred to Eppendorf tubes containing 575 ul of isopropanol, and again precipitated for 10 minutes at room temperature. The tubes were then spun for 45 seconds in a microfuge, the supernatants were discarded and the pellets were air-dried. The pellets were then dissolved in 500 ul of 10 mM Tris, 1 mM EDTA, pH 8.0, containing 100 ug/ml RNase and incubated for 1 hour at 37° C. to digest the RNA. The DNA was precipitated once more by the addition of 50 ul of 5M NaCl followed by 350 ul of isopropanol. After 10 minutes at room temperature, the DNA was spun down by centrifugation for 45 seconds, the supernatants were discarded and the pellets were redissolved in 150 ul of 10 mM Tris 1 mM EDTA, pH 8.0. The plasmid minipreps were subsequently analyzed by digestion with FnuDI and HindIII.

9. FnuDI Methylase Gene Clones: Eight of the 14 plasmids analyzed were found to be sensitive to HaeIII digestion and to carry diverse fragments of *F.nucleatum* D DNA. These plasmids were discarded. The remaining 6 plasmids were found to be resistant to HaeIII digestion and to carry a 5.5 Kb HindIII fragment in common. These plasmids, typical of which is pFnuDIRM 2-33, appeared to be identical. Several of them were chosen and were shown to encode not only the FnuDI modification methylase but also the FnuDI restriction endonuclease.

Figure 3:
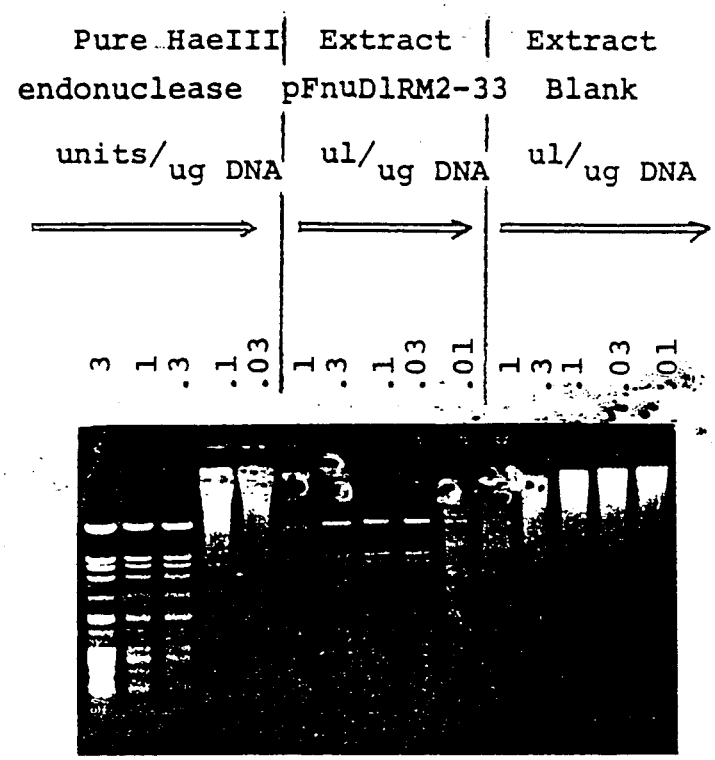
FIG. 3 is a photograph of an agarose gel demonstrating FnuDI restriction endonuclease activity in a cell extract of *E.coli* RR1 (ATCC 31343) carrying pFnuDIRM 2-33.

10. FnuDI Restriction Gene Clone: pFnuDIRM 2-33, and similar plasmids, were found to encode and express the FnuDI restriction endonuclease by assaying extracts of *E.coli* RR1 that carried the plasmids. 50 ml cultures of the clones were grown overnight at 37° C. in L-broth containing 100 ug/ml ampicillin. The cultures were centrifuged at 5K rpm for 5 min and the cell pellets were each resuspended in 3 ml of cell lysis buffer (10 mM Tris pH 7.5, 10 mM mercaptoethanol, 0.1 1 MM EDTA). 0.5 ml of 10 mg/ml lysozyme in the same buffer was added to each and the suspensions were left on ice for 2 hr. The suspensions were frozen overnight at −20° C., then thawed on ice and 3.5 ml of cell lysis buffer containing 0.005% Triton X-100 was vigorously mixed in to each to induce cell lysis. The lysed solutions were microcentrifuged for 5 min to compress the nucleic acids and the supernatants were assayed for endonuclease activity in the following way:

35 ug of phage lambda DNA was diluted into 700 ul of restriction endonuclease digestion buffer (section 2). The solution was dispensed into 6 tubes, 150 ul into the first tube and 100 ul into each of the remaining 5 tubes. 7.5 ul of the extract was added to the first tube to achieve 1 ul extract/ug DNA. 50 ul was then removed from the first tube and transferred to the second tube to achieve 0.3 ul/ug. 50ul serial transfers were continued into tubes number 3 (0.1 ul/ug), 4 (0.03 ul/ug) and 5 (0.001 ul/ug). the sixth tube received no extract and served as a negative control. The tubes were incubated at 37° C. for one hour, then 20 ul from each was analyzed by gel electrophoresis. The extracts were found to contain approximately $3 \times 10^4$ units of FnuDI restriction endonuclease per ml, which corresponds to about $1 \times 10^6$ units per gram of cells (FIG. 3).

11. Transfer of the 5.5Kb fragment to pUC19: 5 ug (50 ul) of purified pFnuDIRM 2-33 DNA was prepared in 100 ul of restriction endonuclease digestion buffer (section 2) containing 20 units of HindIII restriction endonuclease. The solution was incubated at 37° C. for 1 hr. then digestion was halted by heating at 72° C. for 12 min. 3 ug (60 ul) of the digested pFnuDIRM 2-33 DNA was mixed with 1.5 ug (7.5 ul) of HindIII-cleaved and dephosphorylated pUC19 (ATCC 37254). 10 ul of 10 X ligation buffer (section 3) and 22.5 ul of sterile distilled water were added to bring the volume to 100 ul. 4 ul of T4 DNA ligase was added and the solution was incubated at 17° C. for 4 hr. The ligation was sterilized by extraction with 15 ul of chloroform, then clarified by brief microcentrifugation.

12.5 ul of the sterile ligation was mixed with 100 ul CaCl$_2$/SSC (section 3) and 200 ul of competent, icecold, *E.coli* RR1. The mixture was incubated at 42° C. for 3 min, then plated onto an L-agar plate containing ampicillin. The plate was incubated overnight at 37° C. The transformants were collected by flooding the plate with 2.5 ml of 10 mM Tris ph 7.5, 10 mM MgCl$_2$ and scraping the colonies together to form a pool. The pool was inoculated into 500 ml of L-broth containing ampicillin, and a plasmid preparation was purified (section 5). 5 ug of the purified plasmid was digested with 40 units of HaeIII restriction endonuclease in 100 ul of restriction endonuclease buffer (section 6). 12.5 ul of the digested DNA was transformed into *E.coli* RR1 (section 7) and survivors were recovered by plating onto L-agar plates containing ampicillin and incubating the plates overnight at 37° C.

Fourteen transformants were picked and screened by the miniprep procedure (section 8) to identify plasmids composed of pUC19 with the 5.5 Kb fragment inserted at the HindIII site. Thirteen of the plasmids were found to possess this structure; they carried the 5.5 Kb fragment and they exhibited complete resistance to HaeIII digestion. Cell extracts of *E.coli* RR1 carrying two of these plasmids, pFnuDIRM 102-1 and pFnuDIRM 102-4, were assayed for FnuDI restriction endonuclease activity. A sample of pFnuDIRM 102-1 has been deposited at the American Type Culture Collection under ATCC Accession No. 40521. The extracts were found to contain approximately $1 \times 10^5$ units of FnuDI restriction endonuclease per ml of extract, which corresponds to $3 \times 10^6$ units/gm cells.

*E.coli* RR1 carrying pFnuDIRM 2-33 or pFnuDIRM 102-1 are the preferred hosts from which the FnuDI restriction endonuclease can be purified. The strains should be grown to stationary phase at 37° C. in a fermenter, in L-broth containing ampicillin. The cells should then be collected by centrifugation and either broken immediately for extract preparation, or stored frozen at −70° C. until it is convenient to do so.

What is claimed as:

1. Isolated DNA coding for the FnuDI restriction endonuclease, wherein the isolated DNA is obtainable from the vector pFnuDIRM 102-1.

2. A recombinant DNA vector comprising a vector into which a DNA segment coding for the FnuDI endonuclease produced by *Fusobacterium nucleatum* D has been inserted.

3. Isolated DNA coding for the FnuDI restriction endonuclease and methylase, wherein the isolated DNA is obtainable from the vector pFnuDIRM 102-1.

4. A cloning vector which comprises the isolated DNA of claim 1.

5. A cloning vector which comprises the isolated DNA of claim 3.

6. The cloning vector of claim 5, wherein the cloning vector comprises pFnuDIRM 102-1.

7. A host cell transformed by the vector of claim 4, 5 or 6.

8. A method of producing FnuDI restriction endonuclease comprising culturing a host cell transformed with the vector of claim 4, 5 or 6 under conditions suitable for the expression of said endonuclease.

* * * * *